US009678091B2

(12) United States Patent
Duden et al.

(10) Patent No.: US 9,678,091 B2
(45) Date of Patent: Jun. 13, 2017

(54) IN SITU MONITORING FOR WASTEWATER TREATMENT SYSTEMS AND THE LIKE (71) Applicant: Stamford Scientific International, Inc., Poughkeepise, NY (US)

(72) Inventors: Eric D. Duden, Poughkeepsie, NY (US); Marc D. Kessman, Mahopac, NY (US); Thomas E. Frankel, Poughkeepsie, NY (US); Seoungil Kang, Poughkeepsie, NY (US); Todd D. Ritter, Poughkeepsie, NY (US)

( * ) Notice: Subject to any disclaimer, the term of this patent is extended or adjusted under 35 U.S.C. 154(b) by 593 days.

(21) Appl. No.: 13/803,073

(22) Filed: Mar. 14, 2013

(65) Prior Publication Data

US 2014/0095115 A1     Apr. 3, 2014

Related U.S. Application Data (60) Provisional application No. 61/708,650, filed on Oct. 2, 2012.

(51) Int. Cl.
  *B01F 3/04*   (2006.01)
  *C02F 3/20*   (2006.01)
  *G01N 35/00*  (2006.01)
  *G05B 15/02*  (2006.01)

(52) U.S. Cl.
  CPC ............ *G01N 35/00* (2013.01); *G05B 15/02* (2013.01); *B01F 3/04241* (2013.01); *B01F 3/04269* (2013.01); *C02F 3/20* (2013.01); *Y10T 137/7722* (2015.04)

(58) Field of Classification Search
  CPC .................................. Y02W 10/15; C02F 3/02
  USPC .......................................................... 702/188
  See application file for complete search history.

(56) References Cited

U.S. PATENT DOCUMENTS

| 4,375,767 | A  | * | 3/1983  | Magori ..................... 73/861.18 |
| RE33,177  | E  | * | 3/1990  | Schmit ................. B01F 3/0412 134/170 |
| 5,741,960 | A  | * | 4/1998  | Payne et al. ................. 73/23.41 |
| 6,568,282 | B1 | * | 5/2003  | Ganzi ........................ 73/861.42 |
| 8,134,462 | B1 | * | 3/2012  | Tran et al. ............... 340/539.26 |
| 8,276,890 | B1 | * | 10/2012 | Kloehn .............. B01F 3/04113 261/122.1 |
| 2004/0199340 | A1 | * | 10/2004 | Kersey et al. .................. 702/50 |
| 2005/0051498 | A1 | * | 3/2005 | Latino et al. ................ 210/739 |
| 2008/0314122 | A1 | * | 12/2008 | Hunaidi et al. ........... 73/40.5 A |
| 2009/0045122 | A1 | * | 2/2009 | Lin .............................. 210/220 |

(Continued)

FOREIGN PATENT DOCUMENTS

WO        2010092569 A1    8/2010
WO    WO 2010092569 A1 *  8/2010

*Primary Examiner* — Gregory J Toatley
*Assistant Examiner* — Michael Dalbo
(74) *Attorney, Agent, or Firm* — Law Offices of Michael L. Wise, LLC (57) ABSTRACT

Aspects of the invention provide a system comprising a data processor, a gas conducting device, and a sensor. The gas conducting device is submerged and transports a gas. The sensor is connected to the gas conducting device, is also submerged, and is operative to determine a characteristic of the gas conducting device or the gas. The sensor is further operative to transmit data representing the characteristic to the data processor. In one or more non-limiting embodiments, the system comprises a wastewater treatment system, and the gas conducting device comprises a pipe or a diffuser.

3 Claims, 12 Drawing Sheets

(56) References Cited

U.S. PATENT DOCUMENTS

| | | | |
|---|---|---|---|
| 2009/0088985 A1* | 4/2009 | Wee ............................... | 702/30 |
| 2009/0112308 A1* | 4/2009 | Kassem ....................... | 623/1.24 |
| 2012/0072196 A1* | 3/2012 | Adams .......................... | 703/10 |
| 2012/0079940 A1* | 4/2012 | Zeller ............... | B01D 67/0041 |
| | | | 95/273 |
| 2012/0085704 A1* | 4/2012 | Jenkins et al. ............... | 210/614 |
| 2013/0220123 A1* | 8/2013 | England ................. | C02F 3/006 |
| | | | 95/271 |

\* cited by examiner

IN SITU MONITORING FOR WASTEWATER TREATMENT SYSTEMS AND THE LIKE

FIELD OF THE INVENTION

The present invention relates generally to telemetry and industrial automation, and, more particularly, to monitoring and control systems for applications that utilize submerged piping to transport gases, such as wastewater treatment systems.

BACKGROUND OF THE INVENTION

Diffusers are conventionally used to support aerobic biological processes in aerated wastewater treatment systems. A diffuser typically comprises a disc-, tube-, or strip-shaped membrane that is constructed of rubber or other similar materials and which is punctured to provide a number of perforations in the form of holes or slits. In operation, pressurized air is sent through these perforations to create a plume of small bubbles. The bubbles rise through the wastewater and, in so doing, provide the surrounding wastewater with the oxygen needed to sustain the desired biological processes occurring therein. The rising bubbles also provide a mixing function.

Figure 1:
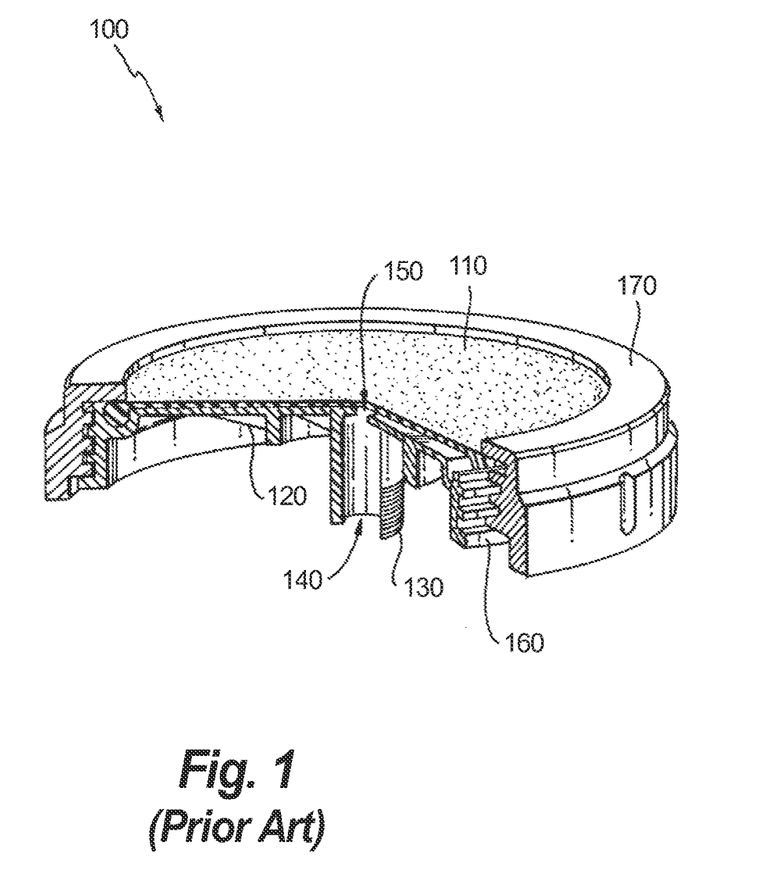
FIG. 1 shows a partially cutaway perspective view of a conventional diffuser unit.

FIG. 1 shows a partially cutaway perspective view of a fine bubble diffuser 100 that might be used in a wastewater treatment facility. Wastewater treatment with such diffusers is described in, as just one example, F. L. Burton, *Wastewater Engineering*, McGraw-Hill College, 2002, which is hereby incorporated by reference herein. In the diffuser 100, a flexible diffuser membrane 110 sits atop a diffuser body 120. The diffuser body comprises a threaded connector 130, an air inlet pipe 140, an orifice 150, and a receiving surface 160 for coupling to a retainer ring 170. The retainer ring 170 holds the flexible diffuser membrane 110 against the diffuser body 120. When gas is applied to the flexible diffuser membrane 110 through the air inlet pipe 140 and the orifice 150, the gas pressure expands the membrane 110 away from the diffuser body 120 and causes the membrane's perforations to open so that the gas discharges through them in the form of fine bubbles. When the gas pressure is relieved, the flexible diffuser membrane 110 collapses on the diffuser body 120 to close the perforations and prevent the liquid from entering the diffuser body 120 in the opposite direction. Generally, a flexible diffuser membrane configured in this way produces bubbles smaller than five millimeters in diameter. The resultant large ratio of surface area to volume in these bubbles promotes efficient oxygen mass transfer between the bubbles and the wastewater.

In use, the above-described diffusers are typically supplied with pressurized air by a network of piping that covers most of the floor of a wastewater treatment tank. In addition to the diffusers, the network of piping may also include ancillary equipment such as moisture purge systems and differential pressure monitoring systems. Nevertheless, a wastewater treatment tank is a harsh and dynamic environment, and piping and diffusers periodically fail as a result. Extreme temperature deviations and the resultant thermal expansion/contraction of thermoplastic parts, as well as unwanted vibrations (e.g., air hammering), may, for example, cause a pipe sidewall, joint, end cap, or support anchor to fail. At the same time, leaks may form in the piping, resulting in undesirable water or sludge buildup inside the network that can drastically affect system efficiency.

While these several failure modes exist in almost every aerated wastewater treatment system, there is a general lack of effective ways of monitoring these systems and detecting small problems early before they turn into catastrophic failures. The typical method of monitoring the health of an installed aeration system consists of looking for: 1) changes in surface bubble and water flow patterns; 2) the existence of water or sludge in a moisture purge line that connects to the network of piping under the surface; 3) an increase in the air pressure required to maintain a given rate of air transport through the network of diffusers; 4) a change in dissolved oxygen in one or more zones of a tank as measured by dissolved oxygen probes; 5) a change in effluent quality as measured by parameters such as biochemical oxygen demand concentration or ammonia concentration; and 6) an increase in air volume required to maintain a steady dissolved oxygen concentration in the wastewater. Nevertheless, these are all macro indicators. In other words, they may indicate serious problems such as diffuser membrane fouling, water or sludge in the pipes, or an aeration system that is otherwise compromised, but, at that point, the problem is already causing disruption to the system performance either in a failure to provide efficient treatment or a failure to provide high quality effluent.

For the foregoing reasons, there is a need for systems and methods for effectively providing early detection of defects in aerated wastewater treatment systems and other systems that utilize submerged pipes for the transport of gases before those defects become more serious failures and result in system disruption.

SUMMARY OF THE INVENTION

Embodiments of the present invention address the above-identified needs by providing monitoring and control systems for applications that utilize submerged piping to transport gases, such as wastewater treatment systems.

Aspects of the invention provide a system comprising a data processor, a gas conducting device, and a sensor. The gas conducting device is submerged and transports a gas. The sensor is connected to the gas conducting device, is also submerged, and is operative to determine a characteristic of the gas conducting device or the gas. The sensor is further operative to transmit data representing the characteristic to the data processor. In one or more non-limiting embodiments, the system comprises a wastewater treatment system, and the gas conducting device comprises a pipe or a diffuser.

In addition, aspects of the invention provide a method for use with a wastewater treatment system or other system that utilizes submerged gas conducting devices such as pipes to transport a gas. Initially, a sensor is connected to a gas conducting device. The gas conducting device and the sensor are then submerged and gas is transported through the gas conducting device. In this condition, the sensor is utilized to determine a characteristic of the gas conducting device or the gas. The sensor subsequently transmits data representing the characteristic to a data processor.

BRIEF DESCRIPTION OF THE DRAWINGS

These and other features, aspects, and advantages of the present invention will become better understood with regard to the following description and accompanying drawings where.

DETAILED DESCRIPTION OF THE INVENTION

The present invention will be described with reference to illustrative embodiments. For this reason, numerous modifications can be made to these embodiments and the results will still come within the scope of the invention. No limitations with respect to the specific embodiments described herein are intended or should be inferred. Moreover, while the illustrative embodiments described herein are directed at applications related to wastewater treatment, aspects of the invention are more generally applicable to any application that utilizes submerged conduits to transport gas.

As used herein, the term "gas conducting device" is meant to encompass any component capable of transporting or conducting a gas. Accordingly, a gas conducting device would include, but not be limited to, a pipe (whether round or otherwise), a pipe coupling, and a diffuser. Moreover, as used herein, the term "submerged" means located under the surface of a liquid, but not necessarily in direct physical contact with that liquid. Finally, the term "connected," as used herein, is intended to mean directly connected (i.e., joined without intervening elements) or indirectly connected (i.e., joined through one or more intervening elements).

Figure 2:
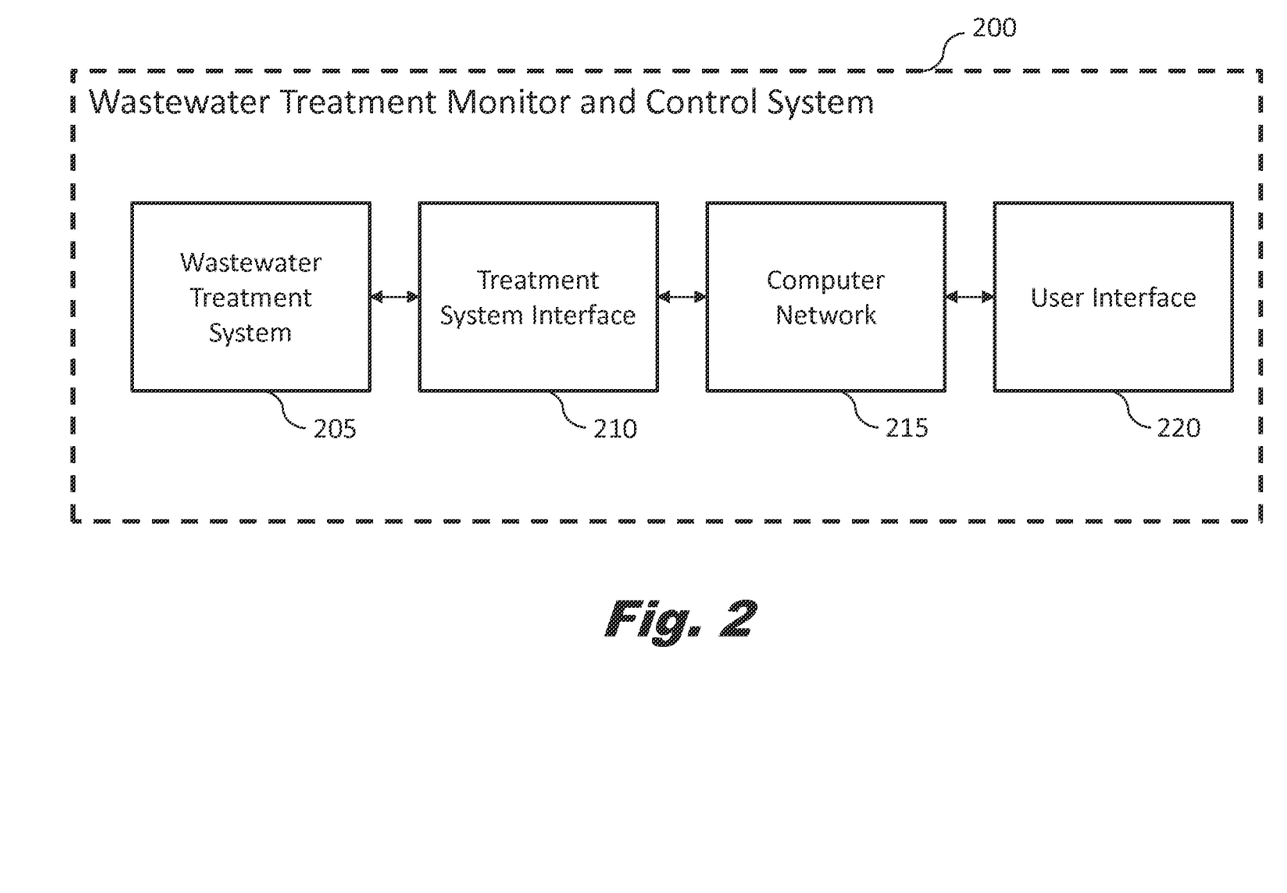
FIG. 2 shows a block diagram of a Wastewater Treatment Monitor and Control System (WTMCS) in accordance with an illustrative embodiment of the invention.

FIG. 2 shows a block diagram of a Wastewater Treatment Monitor and Control System (WTMCS) 200 in accordance with an illustrative embodiment of the invention. The WTMCS 200 can be conceptually broken into several subsystems: a wastewater treatment system 205, a treatment system interface 210, a computer network 215, and a user interface 220. Each of these subsystems is further described below.

Figure 3:
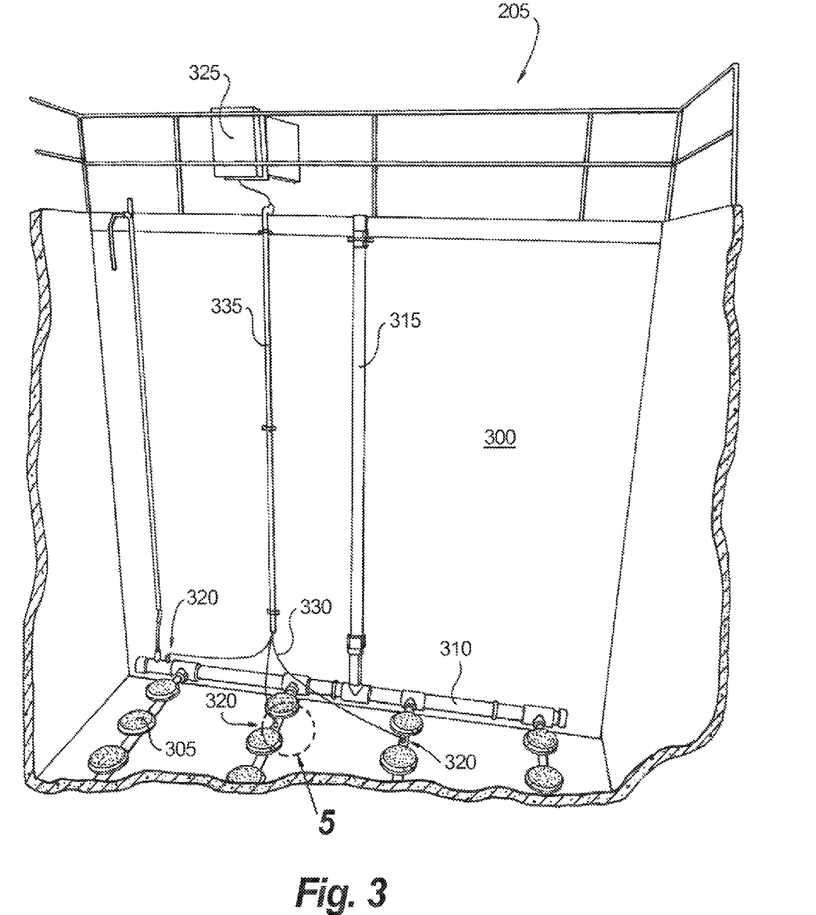
FIG. 3 shows a partially cutaway perspective view of a portion of a first illustrative wastewater treatment system for use in the FIG. 2 WTMCS.

FIG. 3 shows a partially cutaway perspective view of a portion of a first illustrative wastewater treatment system 205 for use in the WTMCS 200. The wastewater treatment system 205 comprises a tank 300 operative to hold wastewater intended for treatment. At the bottom of the tank 300, a plurality of diffusers 305 are supported by, and in gaseous communication with, a network of pipes 310. These pipes 310 are supplied with pressurized air via a vertical down tube 315. Once properly pressurized, the diffusers 305 emit plumes of small bubbles into the wastewater (see Background). In the present embodiment, the diffusers 305 are disk-shaped fine bubble diffusers similar to the fine bubble diffuser 100 shown in FIG. 1, but in other embodiments, the diffusers 305 may just as easily be tubular, strip-shaped, or of another variant.

Figure 4:
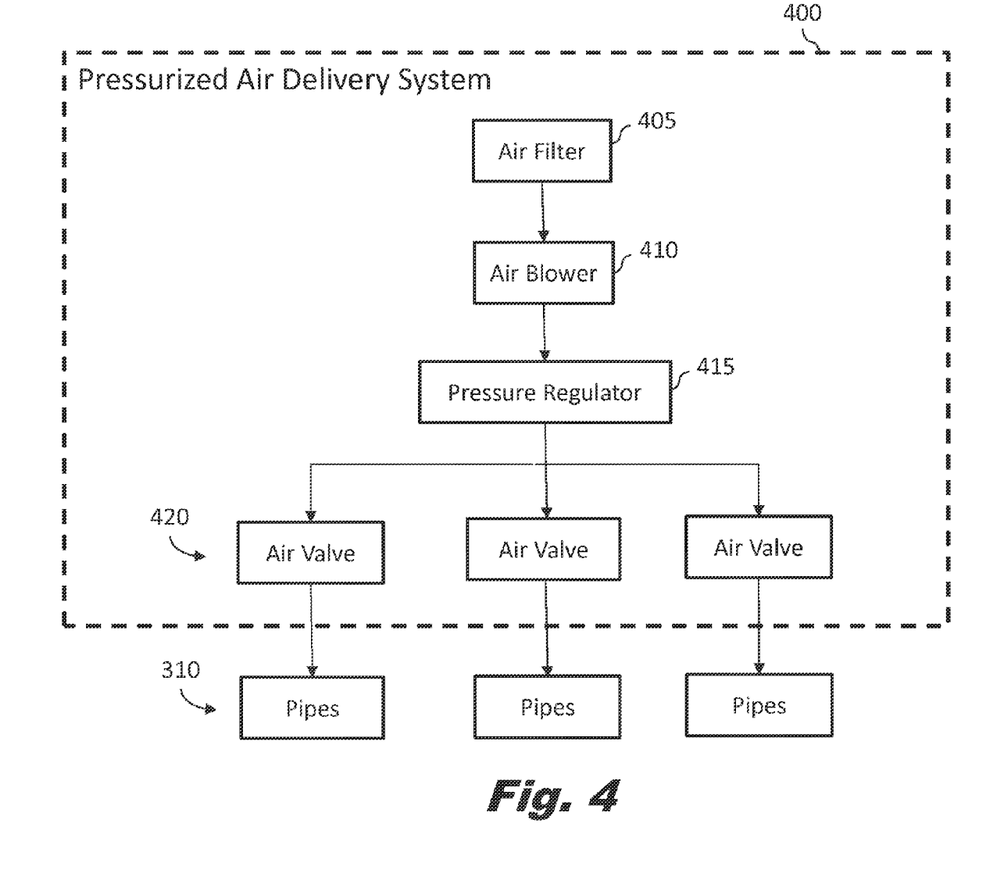
FIG. 4 shows a block diagram of an illustrative pressurized air delivery system for use in the FIG. 3 wastewater treatment system.

The pressurized air is delivered to the distribution pipes 310 of the wastewater treatment system 205 via a pressurized air delivery system. FIG. 4 shows a block diagram of an illustrative pressurized air delivery system 400 for use in the wastewater treatment system 205. In this particular, non-limiting embodiment, air is filtered by an air filter 405 and then pressurized by an air blower 410. After leaving the air blower 410, the pressurized air is transported to a pressure regulator 415, which acts to set the pressurized air at a predetermined pressure. The pressure-regulated pressurized air is then distributed to a set of separately controllable air valves 420. The air valves 420 are preferably fitted with valve actuators, which allow them to be controlled in an automated manner (e.g. electric, pneumatic, hydraulic). Such actuated valves are commercially available from, as just one illustrative source, PetroChem Valve, Inc. (Alvin, Tex., USA). In the present example, only three such air valves 420 are shown, but this number is merely illustrative and any number of air valves may ultimately be utilized when reducing aspects of the invention to practice. The air valves 420 determine how the pressurized air is distributed between several different grids of the pipes 310, which act to define separately regulatable aerobic zones within the tank 300 of the wastewater treatment system 205. In this manner, a portion of the tank 300 can be maintained at a greater or lower volumetric flow rate of pressurized air than another portion, ultimately providing finer control of the wastewater treatment process.

Figure 5:
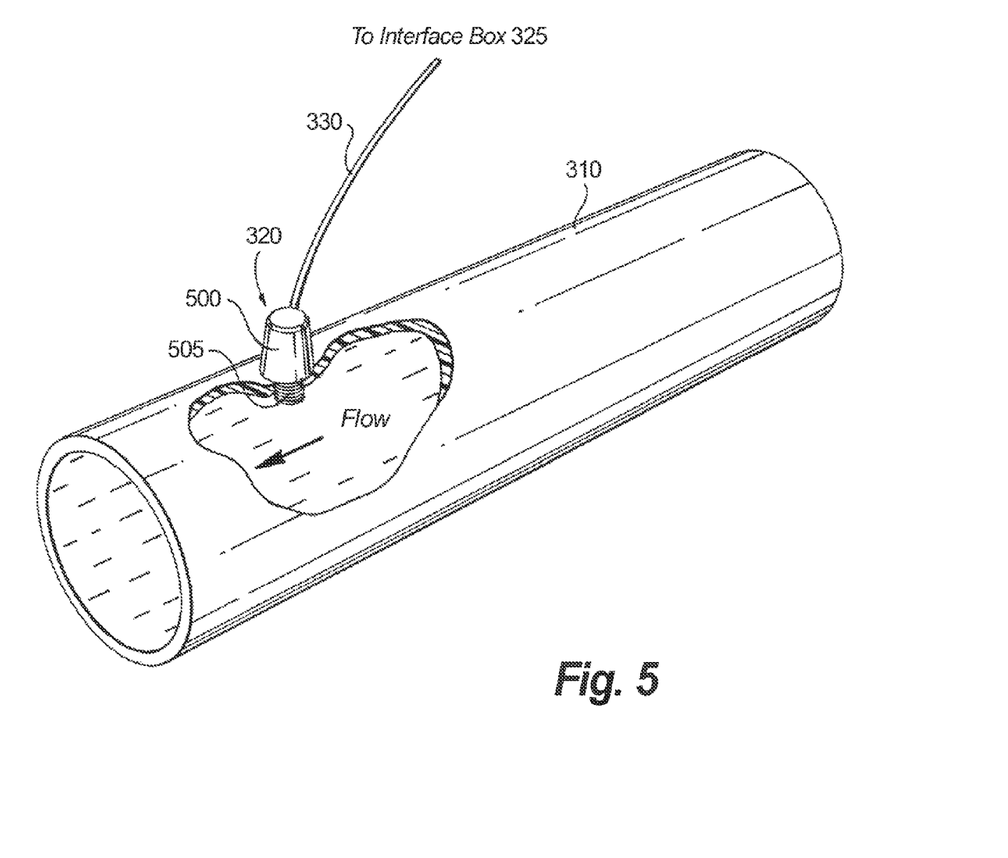
FIG. 5 shows a partially cutaway perspective view of an illustrative sensor for use in the FIG. 3 wastewater treatment system.

Referring again to FIG. 3, several sensors 320 are coupled to the pipes 310 in the tank 300. Each sensor 320 is in data communication with an interface box 325 via a respective signal/power wire 330, which is routed to an interface box 325 via a wire conduit 335 located on the side of the tank 300. Here again, just three illustrative sensors 320 are shown, but in actual reduction to practice, a substantially different number of sensors 320 (e.g., many more than three) may be utilized. FIG. 5 shows a partially cutaway perspective view of a representative one of the sensors 320 mounted to the pipe 310. The sensor 320 comprises a dome-shaped, waterproof housing 500 that encapsulates sensor circuitry within (not visible). The signal/power wire 330 emanates from the top of the housing 500. At the bottom of the housing 500, a threaded attachment point 505 allows the sensor 320 to be readily coupled to oppositely threaded holes in the pipe 310. In this manner, the housing 500 of the sensor 320 is disposed outside the pipe 310, but the sensor 320 is operative to measure characteristics occurring inside the pipe 310. Elastomeric O-rings or other means of obtaining a watertight seal can be used as necessary. In addition, rather than utilizing threads for attachment, several other attachment means may be utilized (e.g., gluing, fusing, solvent welding, clamping, bolting), which will be readily apparent to one skilled in the art.

The sensors 320 are variously operative to determine a characteristic of the pipes 310 or the gas that is transported through the pipes 310. These characteristics include, but are not limited to, temperature, pressure, vibration (e.g., count and severity), relative humidity, gas velocity, gas volume, and gas composition. Process measurements via telemetry are generally described in D. O. deSa, *Instrumentation Fundamentals for Process Control*, Taylor and Francis, 2001, which is hereby incorporated by reference herein. Moreover, suitable sensor circuitry for the applications described herein is commercially available. One source is, for example, Omega Engineering Inc. (Stamford, Conn., USA). Another source is, as another example, Honeywell Sensing and Control (Golden Valley, Minn., USA).

Figure 6:
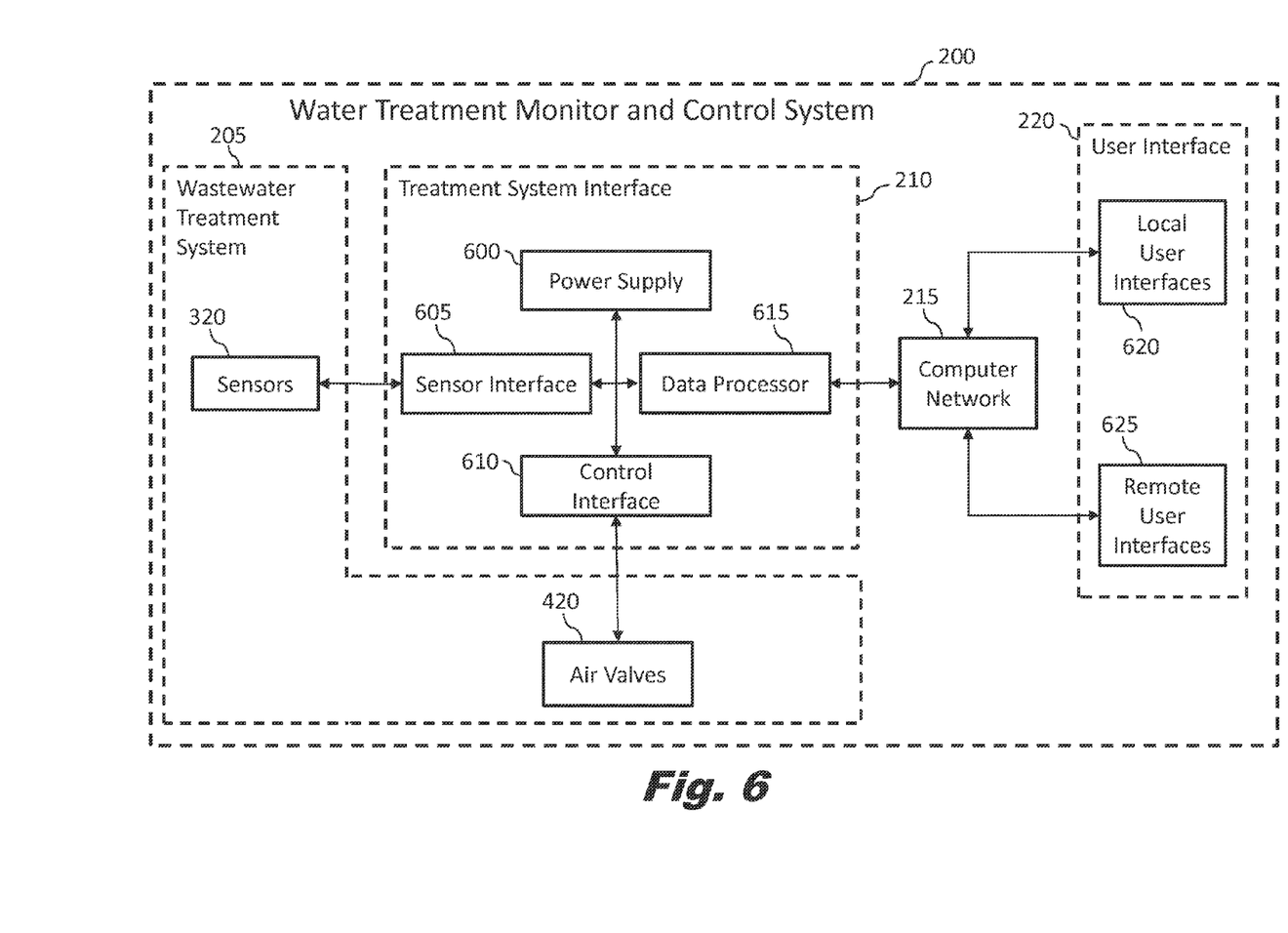
FIG. 6 shows another block diagram of aspects of the FIG. 2 WTMCS.

FIG. 6 provides a block diagram that reveals additional aspects of the illustrative WTMCS 200. The treatment system interface 210 can be conceptually separated into a power supply 600, a sensor interface 605, a control interface 610, and a data processor 615. In the present exemplary embodiment, these elements are physically located in the interface box 325 positioned proximate to an edge of the tank 300 (FIG. 3), although such positioning is by no means limiting. The sensor interface 605 receives the data signals from the sensors 320 via the signal/power wires 330 and, in return, provides power to the sensors 320 that is generated by the power supply 600. The sensor interface 605 may also amplify, digitize, and otherwise modify the data signals as required. Additionally, if some or all of the data signals are multiplexed, the sensor interface 605 may perform any required demultiplexing. Once the data signals from the sensors 320 are properly conditioned, the sensor interface 605 sends the data to the data processor 615.

Figure 7:
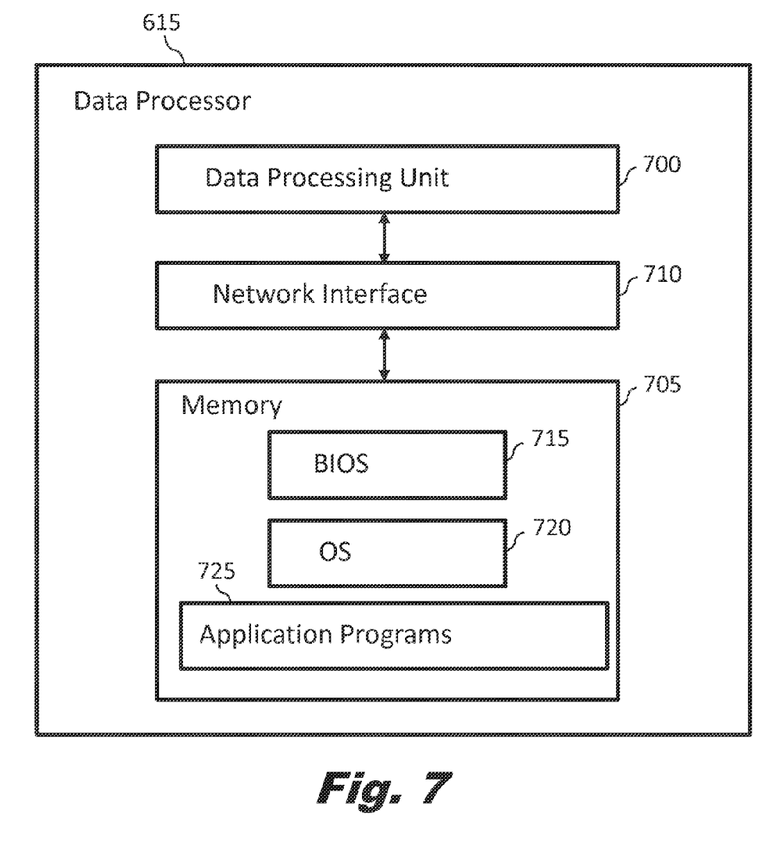
FIG. 7 shows a block diagram of an illustrative data processor in the FIG. 2 WTMCS.

Additional aspects of the data processor 615 are shown in a block diagram in FIG. 7. The data processor 615 comprises a data processing unit 700, a memory 705, and a network interface 710. The memory 705 (non-volatile and/or volatile) stores a basic input/output system (BIOS) 715, an operating system (OS) 720, and application programs 725. Some of the application programs 725, when executed by the data processing unit 700, preferably allow the data processor 615 to act as a web server. A web server is capable of receiving conventional Hypertext Transfer Protocol (HTTP) requests from a remote computing device and providing a HTTP response to that computing device over a suitable Internet Protocol (IP) network connection. This functionality allows the uploading and downloading of documents, application programs, and raw data to and from the data processor 615. Data may be provided in several formats including in an extensible markup language (XML) format. Web servers are widely implemented in computers and computer-like devices, and thus their implementation in the data processor 615 will be familiar to one skilled in the art. Details of configuring a web server are also provided in L. Shklar et al., *Web Application Architecture: Principles, Protocols and Practices*, Wiley, 2003, which is hereby incorporated by reference herein.

Returning back to FIG. 6, the data processor 615 transmits its information to the computer network 215 (e.g., the Internet) via the network interface 710. Data transmission from the data processor 615 to the computer network 215 may be by wires, wirelessly, or some combination of the two. A wired connection may, for example, comprise an Ethernet connection. Wireless communication may comprise communication by, for example, a Wi-Fi, cellular, or satellite connection.

In addition to supplying power to the sensors 320, the power supply 600 may also supply power for the sensor interface 605, the control interface 610, and the data processor 615. While it is contemplated that the power supply 600 will predominantly run on line power, it may also be fitted with one or more batteries that can continue to power the treatment system interface 210 and sensors 320 in case line power is lost.

The user interface 220 comprises local user interfaces 620 and remote user interfaces 625. These user interfaces 620, 625 may access the data available on the computer network 215 to provide a local or remote user with essentially real-time diagnostics about the functioning of the wastewater treatment system 205. Each of the user interfaces 620, 625 may comprise any device or devices capable of accessing the information provided by the data processor 615. They may therefore include, for example, personal computers, laptop computers, tablet computers, cellular telephones with web-browsing capabilities, and the like. Data can be displayed on the user interfaces 620, 625 via browser programs that access the web content (e.g., web pages) provided by the data processor 615. In addition, or alternatively, purpose-specific software programs running on the local and remote user interfaces 620, 625 can display the desired information. In the latter case, application programming interfaces (APIs) and software development kits (SDKs) are preferably made available to software developers so that these developers can create state of the art applications that facilitate and leverage upon the data made available by the sensors 320.

With the real-time diagnostics of a wastewater treatment system 205 available from the sensors 320, it becomes possible to utilize that sensor data not just for diagnostic and predictive purposes, but also to allow the data processor 615 to actually control the wastewater treatment system 205 in response to the diagnostics. Accordingly, additional application programs 725 in the data processor 615 preferably allow the data processing unit 700 to analyze the sensor data and to issue control commands to automated hardware within the WTMCS 200 in response to that data. Communication between the data processor 615 and the automated hardware is via the control interface 610 (FIG. 6), which acts to convert digital commands received from the data processor 615 into appropriate control signals for the automated hardware. If it is assumed, for example, that the WTMCS 200 comprises actuated air valves 420 like those described with reference to FIG. 4, the control interface 610 may send signals to these automated air valves 420 over an analog loop (e.g., using the 4-20 mA analog signaling protocol) or over a digital loop (e.g., using a Foundation Fieldbus, Profibus, DeviceNet, Hart, or Pakscan digital network). Automation of a valves and the like is commonly utilized in industrial applications and is described in, for example, T. L. M. Bartelt, *Industrial Automated Systems: Instrumentation and Motion Control*, Cengage Learning, 2010, which is hereby incorporated by reference herein. The data processor 615 can thereby control the various aerobic zones of the wastewater treatment system 205 in response to real time diagnostic information received from the sensors 320. Moreover, because the data processor 615 is also operative to communicate with remote users via the remote user interfaces 625, the WTMCS 200 gives remote users the ability to control the wastewater treatment system 205, to at least some extent, while located away from the physical plant.

Figure 8:
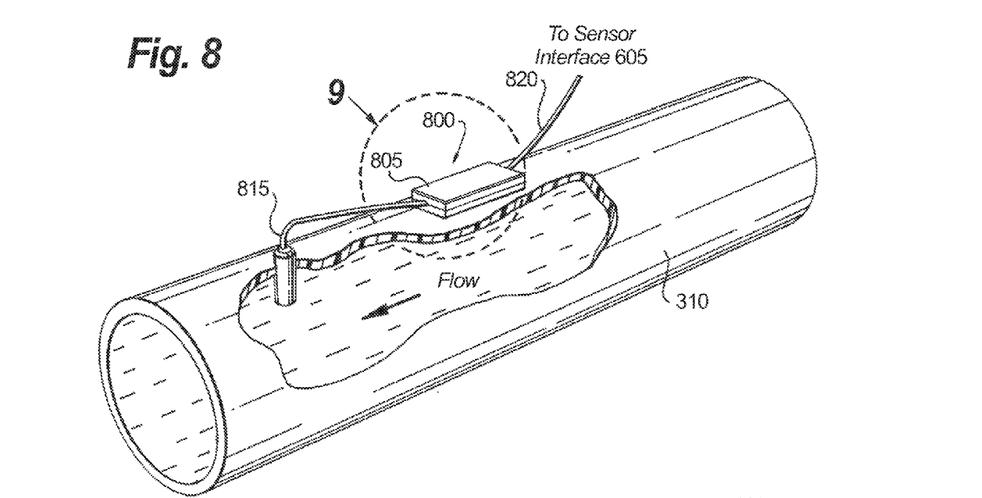
FIG. 8 shows a partially cutaway perspective view of an alternative illustrative sensor for use in the FIG. 3 wastewater treatment system.
Figure 9:
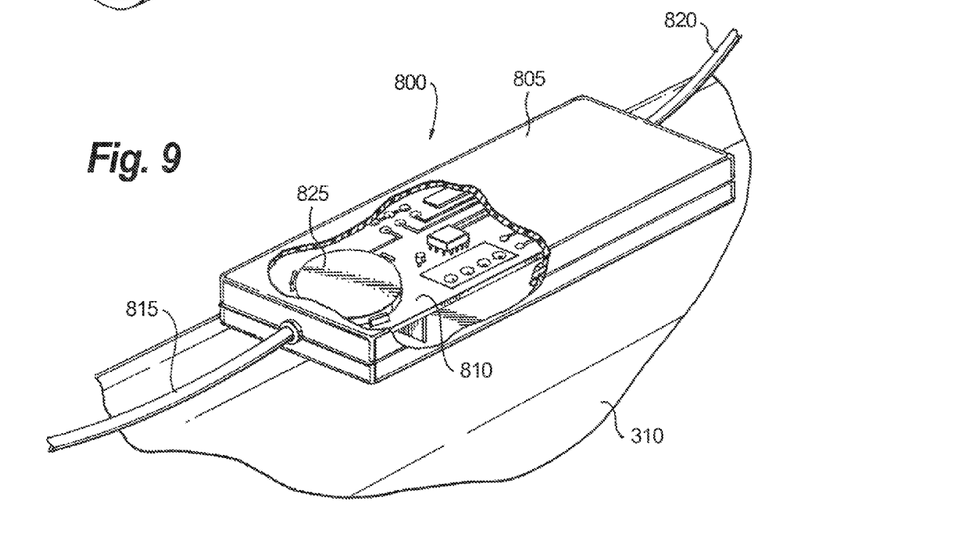
FIG. 9 shows a close-up partially cutaway perspective view the FIG. 8 alternative sensor.

While the illustrative embodiment described above utilizes a particular sensor configuration (FIG. 5), there are many alternative sensor configurations that may also be utilized to measure characteristics of submerged piping or the gases transported therein, and these many alternative configurations would also fall within the scope of the present invention. FIGS. 8 and 9, show, for example, an alternative form of wired sensor 800 for use in the wastewater treatment system 205, with FIG. 8 showing a partially cutaway perspective view of the sensor 800 attached to the pipe 310, and FIG. 9 showing a close-up partially cutaway perspective view of the sensor 800 itself. In this illustrative embodiment, the sensor 800 comprises a waterproof rectangular housing 805, which encases sensor circuitry 810 and from which emanate a probe 815 and a signal/power wire 820. The probe 815 may comprise an actual sensory element (e.g., a thermocouple to allow a temperature measurement) or may alternatively comprise a conduit that is operative to deliver a portion of the gas inside the pipe 310 to the sensor circuitry 810 (to allow, e.g., a pressure measurement). The sensor circuitry 810 comprises a battery 825, which allows it to supply its own power, thereby eliminating the need to supply power to the sensor 800 from the treatment system interface 210, if so desired. The housing 805 is adhered to the outside of the pipe 310 by gluing, fusing, solvent welding, clamping, bolting, or another method of fixation. The distal end of the probe 815, in turn, is passed into the interior of the pipe 310 via an aperture in the pipe wall, which is subsequently sealed around the probe 815 to prevent leakage. In accordance with aspects of the invention, the housing 805 and sensor circuitry 810 are thereby disposed on an outside surface of the pipe 310, while the probe 815 is at least partially disposed inside the pipe 310. Finally, the signal/power wire 820 is directed upward to the sensor interface 605 of the treatment system interface 210 in a manner similar to that shown in FIG. 3 for signal/power wires 330.

Other alternative forms of sensors may communicate with the treatment system interface 210 wirelessly and, when internally powered by batteries, thereby eliminate the need to provide any form of wiring between the sensors and the remainder of the WTMCS 200. Advantageously, a wireless sensor system may be more robust than a wired system in the harsh environment of a wastewater treatment system and other submerged systems, and may also act to reduce installation complexity and costs.

Figure 10:
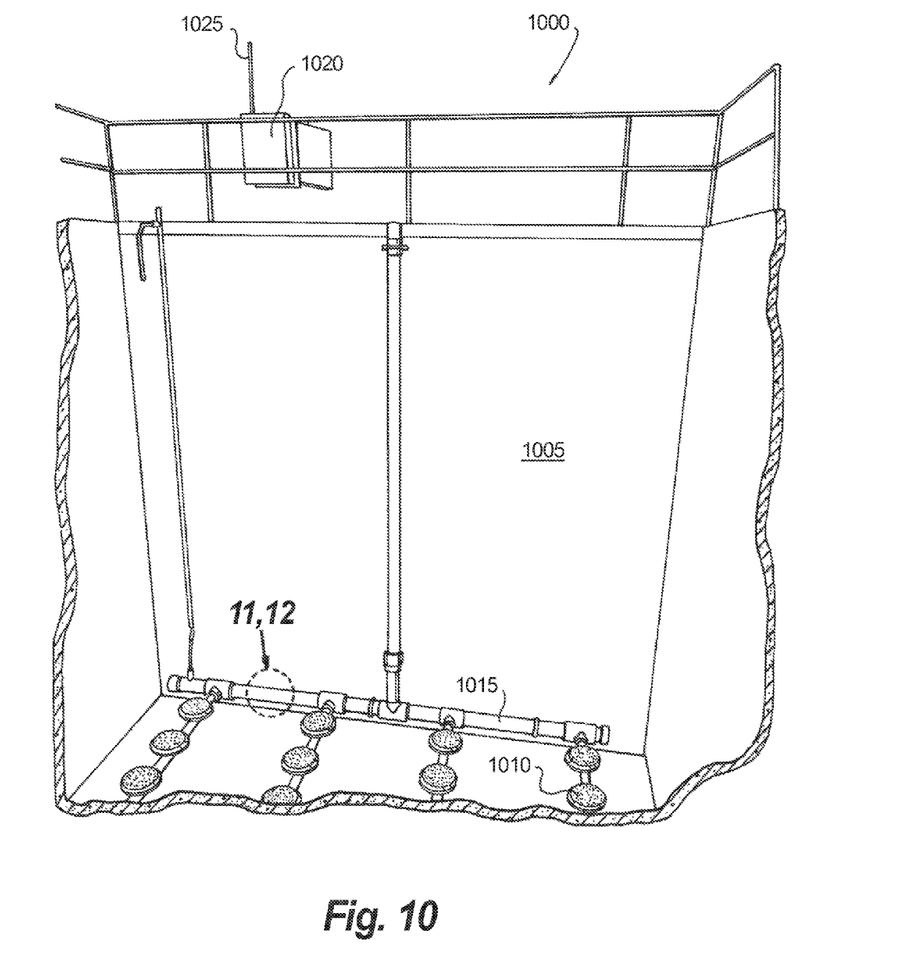
FIG. 10 shows a partially cutaway perspective view of a portion of a second illustrative wastewater treatment system for use in the FIG. 2 WTMCS.

FIG. 10 shows a partially cutaway perspective view of a portion of a second illustrative wastewater treatment system 1000 for use in the WTMCS 200. Like before, the wastewater treatment system 1000 comprises a tank 1005 operative to hold wastewater intended for treatment. At the bottom of the tank 1005, a plurality of diffusers 1010 are supported by, and in gaseous communication with, a network of pipes 1015. Finally, an interface box 1020 is located proximate to the side of the tank 1005 and contains the treatment system interface 210. However, unlike the previously described wastewater treatment system 205, the present wastewater treatment system 1000 is devoid of any wires between sensors and the interface box 1020. Instead, the sensors are wireless, and the interface box 1020 is fitted with an antenna 1025 for receiving data signals from the wireless sensors.

Figure 11:
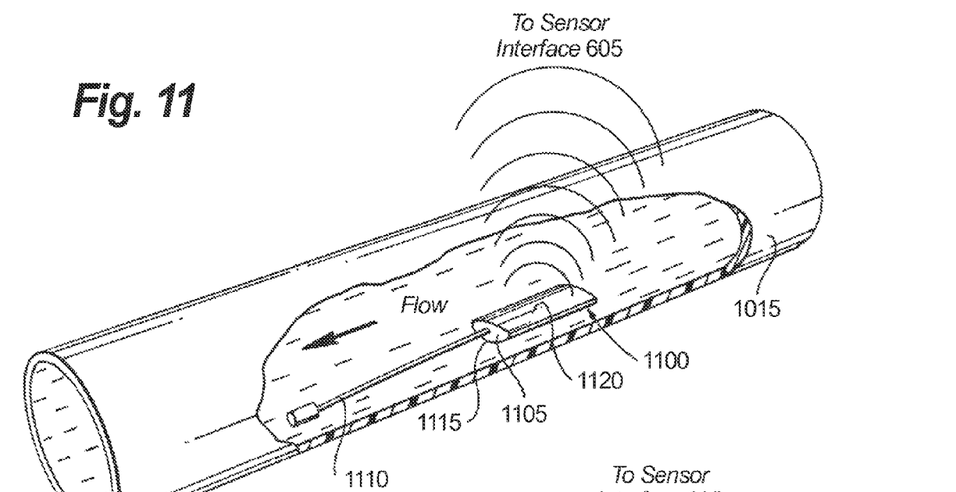
FIG. 11 shows a partially cutaway perspective view of an illustrative sensor for use in the FIG. 10 wastewater treatment system.

FIG. 11 shows a partially cutaway perspective view of an illustrative wireless sensor 1100 for use in the wastewater treatment system 1000. The sensor is mounted on the pipe 1015. The sensor 1100 again comprises a housing 1105 and a probe 1110. In this particular exemplary embodiment, moreover, an antenna is also present to facilitate wireless communication, but is not visible because it is part of the sensor circuitry and is therefore contained within the housing 1105. In alternative embodiments, however, an external antenna wire emanating from the housing 1105 may also be utilized. The sensor 1100 is mounted on an inside surface of the pipe 1015 (by, e.g., gluing, fusing, solvent welding), making the sensor 1100 entirely disposed within the pipe 1015. Moreover, for purposes of mounting the sensor 1100 to the inside surface of the pipe 1015 and reducing any interference between the sensor 1100 and the gas flow within the pipe 1015, the housing 1105 of the sensor 1100 includes a first housing surface 1115 and a second housing surface 1120 that each describes a different respective radius of curvature. In one or more embodiments of the invention, one housing surface may, as just one example, have a two-inch radius of curvature while the other housing surface has a 1.5-inch radius of curvature. This allows the housing 1105 to define curved surfaces that substantially follow the inside curvature of many commonly utilized pipes (e.g., pipes with four-inch and three-inch diameters, respectively). The conformance between the shape of the first housing surface 1115 and the contour of the inside wall of the pipe 1015 to which it is adhered is illustrated in FIG. 11. Notably, with the antenna for the sensor 1100 within the pipe 1015 itself, wireless communication is operative to predominantly take place through the gas within the pipe 1015 as opposed to through the outside liquid (e.g., wastewater), where radio propagation may be adversely affected.

Figure 12:
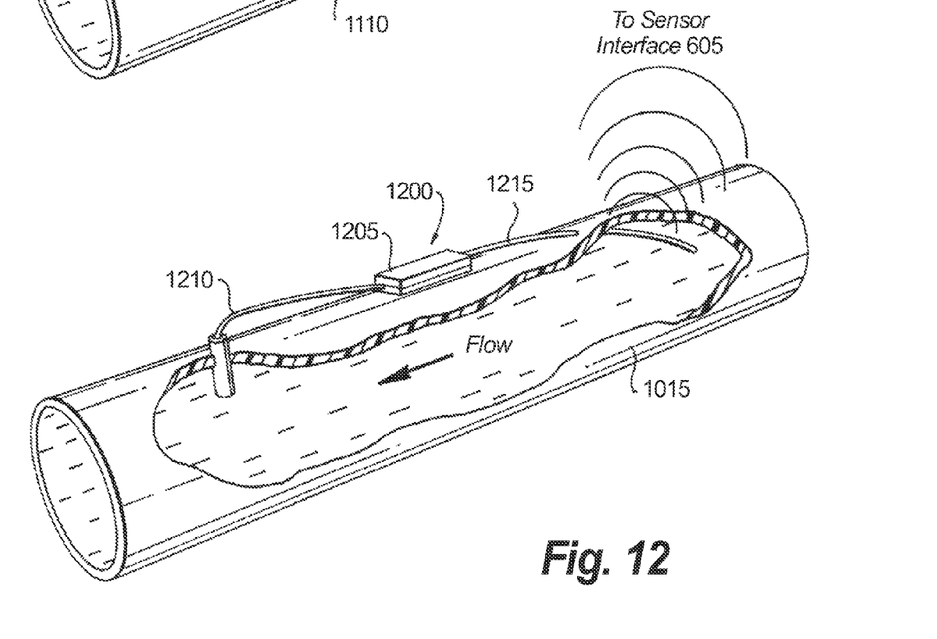
FIG. 12 shows a partially cutaway perspective view of an alternative illustrative sensor for use in the FIG. 10 wastewater treatment system.

FIG. 12 shows a partially cutaway perspective view of an alternative illustrative wireless sensor 1200 for use in the wastewater treatment system 1000 with the sensor 1200 attached to the pipe 1015. Here again, the sensor 1200 is wireless, meaning that it does not require wiring to the sensor interface 605 of the treatment system interface 210 for signal communication and power. The sensor 1200 has many similarities with the wired sensor 800 shown in FIGS. 8 and 9. The sensor 1200 includes a housing 1205 (with sensor circuitry therein) and a probe 1210. Moreover, the housing 1205 of the sensor 1200 is also mounted to the outside of the pipe 1015, while the probe 1210 is partially disposed within the pipe 1015 after being passed through an aperture in the pipe 1015. However, unlike the previously described wired sensor 800, the present sensor 1200 does not include a signal/power wire but instead comprises an antenna 1215 that facilitates wireless communication. Like the probe 1210, the antenna 1215 is also passed into the pipe 1015 through a sealed aperture in the pipe wall so that a portion of the antenna 1215 is disposed within the pipe 1015. Accordingly, even though the housing 1205 is disposed on the outside of the pipe 1015, the sensor 1200 is still able to transmit radio data into a gas rather than into a liquid via the portion of the antenna 1215 within the pipe 1015.

Although not limiting, the wireless sensors 1100, 1200, and more generally, wireless sensor embodiments in accordance with aspects of the invention, may utilize a radio frequency identification (RFID) technology in combination with suitable sensor circuitry and probes. The combination may then transmit their measurement data along with identifying information that identifies the sensors. RFID sensor technology is described in, for example, A. Rida et al., *RFID-Enabled Sensor Design and Applications*, Artech House, 2010, which is also hereby incorporated by reference herein. Suitable equipment may be obtained from several vendors including, for instance, GAO RFID Inc. (Toronto, ON, Canada) and Phase IV Engineering, Inc. (Boulder, Colo., USA).

Embodiments of the present invention provide a number of advantages. A monitor and control system in accordance with aspects of the invention may, for example, allow the kind of automated sensor-based wastewater treatment system control and optimization described above. If, for instance, air velocity sensors indicate that one aerobic zone is experiencing a lower volumetric flow rate of air than desired, a data processor may command that an air valve for that lower-performing aerobic zone be modified to increase its flow rate. In addition, several automated air valves may be coordinated to automatically maintain a desired pattern of dissolved oxygen in the wastewater being treated.

At the same time, a properly distributed array of sensors in a wastewater treatment system may also predict failures, detect failures, and determine maintenance requirements. Air velocity sensors, for example, may help to determine the air distribution uniformity in the system's piping network and thereby allow optimization of pipes and perforation sizes in diffusers to improve efficiency. Temperature sensors may determine the actual temperature of a piping network so as to ascertain if the piping is staying within a safe operating range. Pressure measurements, including those taken near where a diffuser attaches to a distribution pipe or in the air inlet pipe of a diffuser itself (see the air inlet pipe 140 in FIG. 1), can determine back pressure requirements for a diffuser and therefore indicate the level of diffuser fouling. Vibration sensors can determine unsafe air hammering and other sources of vibration that can cause pipe failures and leakage (e.g., broken mounting brackets). Relative humidity measurements can detect water and sludge in the pipes, which is a particular concern in those wastewater treatment systems were the pressurized air is frequently cycled on and off. Lastly, gas composition sensors can indicate the composition of the pressurized air carried in the pipes (e.g., oxygen content).

In addition, it may be particularly beneficial to correlate the real-time data provided by sensors in or on the piping of a wastewater treatment system with other real time measurements, such as dissolved oxygen and off-gas respirometry measurements. As the name would suggest, dissolved oxygen measurements determine the amount of oxygen dissolved in wastewater. Off-gas respirometry, in contrast, utilizes one or more hoods located over the surface of wastewater to analyze the gases emitted by that wastewater. Combined, the sensor, dissolved oxygen, and off-gas respirometry data allow one to precisely determine and optimize those factors that affect oxygen transfer efficiency and oxygen uptake rates.

Figure 13:
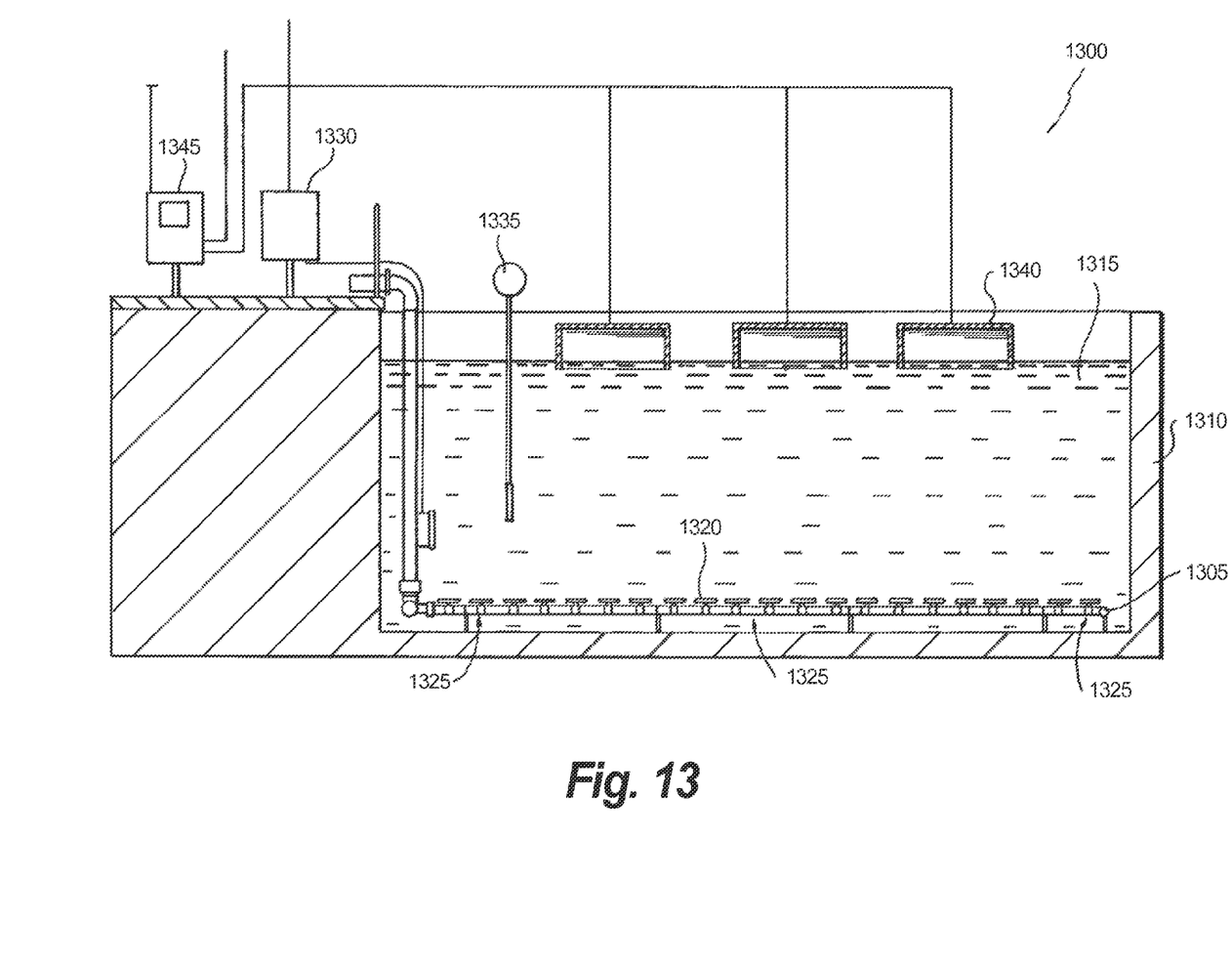
FIG. 13 shows a partially cutaway elevational view of a portion of a wastewater treatment system in accordance with an illustrative embodiment of the invention with various types of sensors in place.

FIG. 13 shows a partially cutaway elevational view of a portion of a wastewater treatment system 1300 in accordance with an illustrative embodiment of the invention with these various types of sensors in place. A network of pipes 1305 at the bottom of a tank 1310 and submerged in wastewater 1315 includes several diffusers 1320 and a plurality of internal wireless sensors 1325 of the type described above with reference to FIG. 11 (marked but not visible because they are inside the pipes 1305). Data from the sensors 1325 is wirelessly sent to an interface box 1330, which houses a treatment system interface similar to the treatment system interface 210 (FIG. 6). At the same time, a dissolved oxygen sensor 1335 determines the amount of oxygen dissolved in the wastewater 1315. Finally, collection hoods 1340 positioned over the surface of the wastewater 1315 collect gases emitted from the wastewater 1315 and direct those gases to a gas analyzer 1345. Ultimately, data from the sensors 1325 is correlated with dissolved oxygen data and off-gas respirometry data to determine the relationships between the various measurements.

It may also be particularly beneficial to utilize aspects of the invention to determine diffuser dynamic wet pressure (DWP) and orifice differential pressure (ODP). DWP indicates the extent of the fouling of a diffuser, and is an important measurement for determining diffuser membrane maintenance (e.g., cleaning) and replacement. ODP allows an operator to approximate the air flow rate per diffuser in an aeration grid.

Figure 14:
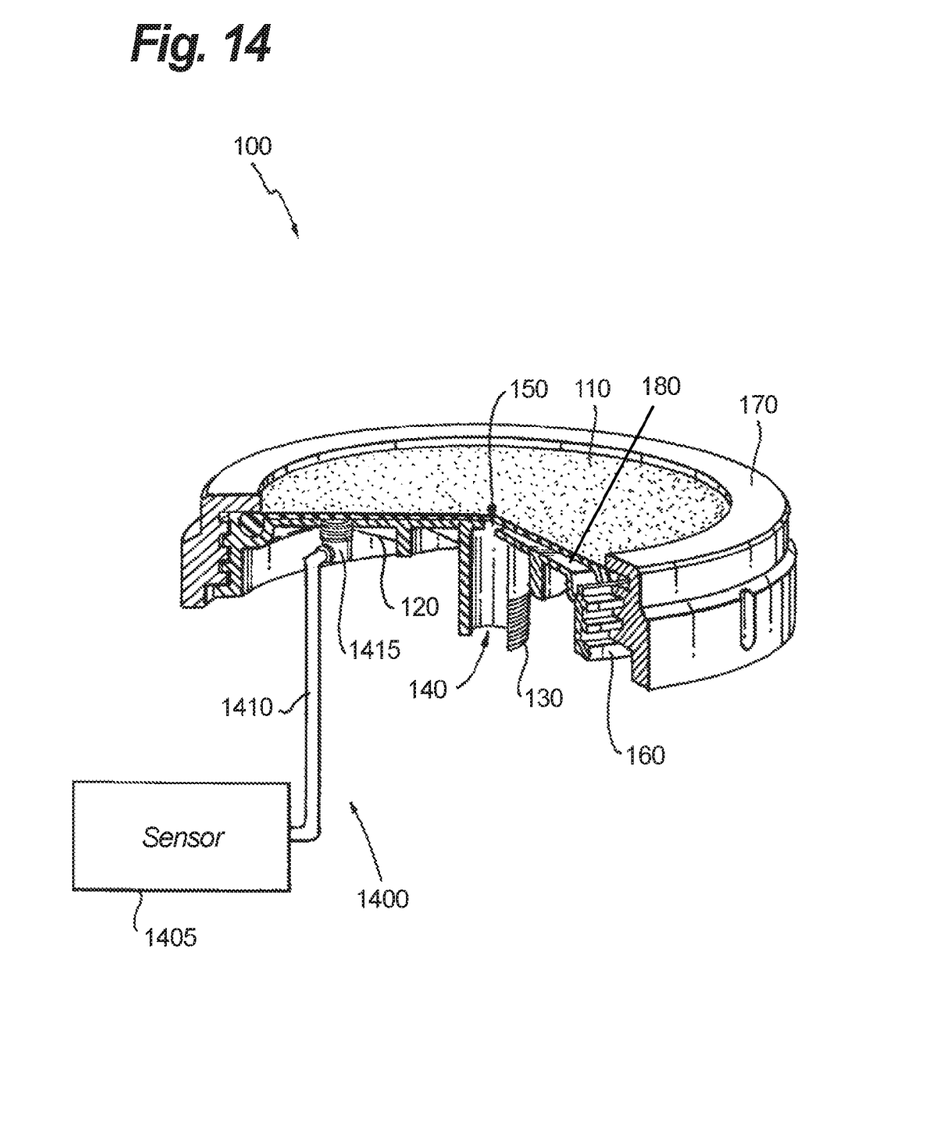
FIG. 14 shows a partially cutaway perspective view of a sensor and a diffuser configured for differential pressure measurements, in accordance with an illustrative embodiment of the invention.

For determining DWP and ODP for a disc diffuser of the type shown in FIG. 1, a gas pressure measurement is preferably taken immediately below (i.e., upstream of) the diffuser membrane, but above (i.e., downstream of) the diffuser's orifice. FIG. 14 shows a partially cutaway perspective view of a sensor 1400 attached to a diffuser 100 in a manner configured for such a measurement, in accordance with an illustrative embodiment of the invention. The diffuser 100 in FIG. 14 contains the same elements as the diffuser 100 shown in FIG. 1, and is therefore labeled with like reference numerals. A flat surface 180 defined by the diffuser body 120 and on which a majority of the diffuser membrane 110 rests when the diffuser membrane 110 is in a relaxed state (i.e., the uninflated state shown in the figure) is also labeled. The sensor 1400, in turn, comprises a sensor housing 1405 (with pressure measuring sensor circuitry within) and a probe 1410, which acts as a gas conduit. The sensor housing 1405 may be mounted on the outside or the inside of a distribution pipe (not specifically shown), and the sensor 1400 may communicate the pressure data to a data processor by wire or wirelessly, as provided in detail above. The probe 1410 is connected to the diffuser 100 by being fixated to an elbow fitting 1415 that passes through the diffuser body 120. The probe 1410 is thereby operative to pass a portion of the gas immediately below the diffuser membrane 1410 to the sensor circuitry so that the sensor circuitry can determine the pressure in that particular location. That is, the sensor 1400 is operative to determine a pressure at a location between the flexible diffuser membrane 110 and the flat surface 180.

Once pressure immediately below the diffuser membrane, $P_{dif}$ is determined by the sensor 1400 while the diffuser 100 is actively producing bubbles in a wastewater treatment tank, $P_{dif}$ may be utilized to determine DWP and ODP. More precisely, to negate the effects of hydrostatic pressure, DWP may be determined by subtracting from $P_{dif}$ the pressure needed to produce bubbles from a bubbler (i.e., a device with substantially zero head loss) located at the same submergence in the wastewater tank as the diffuser membrane. ODP, in turn, may be determined by measuring the pressure in the distribution pipe feeding the diffuser 100 and subtracting $P_{dif}$ from that distribution pipe pressure. In both cases, aspects of the invention thereby allow an operator to readily measure important parameters indicative of wastewater treatment system performance.

In closing, it should again be emphasized that the above-described embodiments of the invention are intended to be illustrative only. Other embodiments can use different types and arrangements of elements, as well as different method steps, for implementing the described functionality. In one alternative embodiment, for example, a suitably small sensor may be entirely located between a diffuser body and diffuser membrane in order to measure pressure characteristics (e.g., pressure) at this location and thereby facilitate the determination of diffuser dynamic wet pressure and orifice differential pressure. These numerous alternative embodiments within the scope of the invention will be apparent to one skilled in the art given the teachings provided herein.

Moreover, all the features disclosed herein may be replaced by alternative features serving the same, equivalent, or similar purposes, unless expressly stated otherwise. Thus, unless expressly stated otherwise, each feature disclosed is one example only of a generic series of equivalent or similar features.

Finally, any element in a claim that does not explicitly state "means for" performing a specified function or "step for" performing a specified function is not to be interpreted as a "means for" or "step for" clause as specified in 35 U.S.C. §112, ¶6. In particular, the use of "step of" in the claims herein is not intended to invoke the provisions of 35 U.S.C. §112, ¶6.

What is claimed is:

1. A system for treating wastewater, the system comprising:
    a data processor;
    a gas conducting device;
    a diffuser body, the diffuser body attached to the gas conducting device, defining a flat surface, and defining a passage in gaseous communication with the gas conducting device;
    a flexible diffuser membrane, a majority of the flexible diffuser membrane resting on the flat surface when the flexible diffuser membrane is in a relaxed state, and the flexible diffuser membrane supported by the diffuser body and in contact with wastewater when the gas conducting device, the diffuser body, and the flexible diffuser membrane are submerged in wastewater; and
    a sensor, the sensor operative to determine pressure at a location between the flexible diffuser membrane and the flat surface, and to transmit data representing the pressure to the data processor.

2. The system of claim 1, wherein the data processor is operative to determine a value indicative of fouling of the flexible diffuser membrane at least in part based on data transmitted from the sensor, and to make the value available to a user.

3. The system of claim 1, wherein the passage defines an orifice narrower than a remainder of the passage.

* * * * *